US005462752A

United States Patent [19]

Chao et al.

[11] Patent Number: 5,462,752
[45] Date of Patent: Oct. 31, 1995

[54] INHIBITION OF PLATELET BINDING

[75] Inventors: Francis C. Chao, deceased, late of Newton, Mass., by Johanna T. Chao, legal representative; Michael S. Chao, heir, New York, N.Y.; Mark S. Chao, heir; Lorraine S. Chao, heir, both of Newton, Mass.

[73] Assignee: PRP, Inc., Watertown, Mass.

[21] Appl. No.: 281,758

[22] Filed: Jul. 28, 1994

[51] Int. Cl.⁶ .......................... A61K 35/14; A61K 37/00
[52] U.S. Cl. .................. 424/532; 424/93.72; 514/822; 514/824
[58] Field of Search ................. 424/532, 93.72; 514/822, 824

[56] References Cited

U.S. PATENT DOCUMENTS

| | | | |
|---|---|---|---|
| 4,666,884 | 5/1987 | Hawiger et al. | 514/13 |
| 5,185,160 | 2/1993 | Chao | 424/532 |
| 5,332,578 | 7/1994 | Chao | 424/532 |
| 5,342,830 | 8/1994 | Scarborough | 514/12 |

Primary Examiner—John W. Rollins
Attorney, Agent, or Firm—Wolf, Greenfield & Sacks

[57] ABSTRACT

Methods for inhibiting the attachment of platelets to a site of an injury are provided. The methods involve administering to a subject that has sustained an injury an effective amount of a platelet binding-site agent. Preferred platelet binding-site agents are platelets that are substantially free of platelet substances contained in lysosomes, dense granules or alpha granules.

17 Claims, No Drawings

INHIBITION OF PLATELET BINDING

FIELD OF THE INVENTION

This invention relates to inhibiting platelets from binding at the sites of vascular injury to avoid adverse health consequences.

BACKGROUND OF THE INVENTION

Injury to the vascular system can lead to a number of undesirable health conditions, including, for example, forms of atherosclerosis and arteriosclerosis. The contribution of the various biological pathways leading to such undesirable health conditions is not fully understood, and prophylaxis against such conditions has been less than fully effective.

A common injury to the vascular system occurs as a side effect of a medical procedure for treating ischemic heart disease. Ischemia refers to a lack of oxygen due to inadequate perfusion of blood. Ischemic heart disease is characterized by a disturbance in cardiac function due to an inadequate supply of oxygen to the heart. The most common form of this disease involves a reduction in the lumin of coronary arteries, which limits coronary blood-flow.

When ischemic heart disease becomes very serious, then management must be invasive. Until recently, ischemic heart disease was treated by coronary-artery, bypass surgery. Less invasive procedures, however, now have been developed. These procedures involve the use of catheters introduced into the narrowed region of the blood vessel ("the stenosis") for mechanically disrupting, laser ablating or dilating the stenosis.

The most widely used method to achieve revascularization of a coronary artery is percutaneous transluminal coronary angioplasty. A flexible guide wire is advanced into a coronary artery and positioned across the stenosis. A balloon catheter then is advanced over the guide wire until the balloon is positioned across the stenosis. The balloon then is repeatedly inflated until the stenosis is substantially eliminated. This procedure, as compared to heart surgery, is relatively noninvasive and can result in hospital stays of only three days. The procedure is an important tool in the management of serious heart conditions.

A serious drawback to angioplasty procedures is the re-occurrence of the stenosis at the site of the angioplasty, or "restenosis". The clinical effects of angioplasty include endothelial denudation, vascular wall damage and rupture of the tunica intima vasorum. These injuries have been found to cause in many cases proliferation of the arterial smooth muscle cells and, it is believed, restenosis. Restenosis may occur in as many as 40% of patients that have undergone an angioplasty procedure.

To date, there is no effective treatment for preventing restenosis. Although the use of drugs such as anticoagulants have been suggested, restenosis still remains the main complication of successful angioplasty procedures.

There has been some attempt to delineate the role that platelets might play in restenosis following angioplasty. Although the role of platelets has remained unclear, it is believed that: (1) platelets are involved in the initiation of smooth muscle proliferation following angioplasty; but (2) through release of platelet derived growth factor, platelets may regulate the movement of smooth muscle cells into the intima following angioplasty. These conclusions were reached based upon studies comparing the response to angioplasty of thrombocytopenic animals to normal animals. The thromobocytopenic animals were depleted of circulating platelets using anti-platelet antibodies. Even if this approach were believed to be capable of preventing restenosis, it would not be a desirable approach in humans, in that it requires depleting circulating platelets. It also might require human or humanized anti-platelet antibodies which presently are not believed to be available.

SUMMARY OF THE INVENTION

The invention in its broadest aspect provides a method for inhibiting the attachment of platelets to a site of an injury. The platelet binding site agents then interfere with physiological events that otherwise would occur as a result of platelet binding. An effective amount of a platelet binding-site agent is administered to a subject who has sustained an injury. The platelet binding-site agent is administered locally to the site of the injury.

Platelet binding-site agents are agents that can bind to the site to which platelets normally bind as a result of injury to a vessel. Platelet binding-site agents can be platelets that are free of a platelet substance such as a growth factor or adhesion factor. Platelet binding-site agents also can be derived from platelets or can be prepared synthetically. Most preferred are binding-site agents that are in preparations containing platelets, or membrane fragments thereof, that have been treated to remove platelet substances such as growth factors and adhesion molecules. One particularly preferred agent is a platelet membrane particle or microvesicle. Platelet membrane particles are compositions comprising a glycoprotein or a phospholipid either separately or in combination. Such particles can take the form of microvesicles.

The platelet binding-site agent may be administered locally to an internal surface of the subject. In one important application of the invention, the platelet bindingssite agent is administered to interfere with the progression of arterial disease. In another important aspect of the invention, the binding-site agent is administered to prevent tissue adhesions resulting from surgery.

In one particularly preferred aspect of the invention the platelet binding-site agent is administered to a subject with a coronary artery occlusion in conjunction with treatment of the occlusion by angioplasty. Most preferably the platelet binding-site agent is administered to a patient in conjunction with a percutaneous, transluminal, balloon-dilatation angioplasty procedure. Such treatments can be for the purpose of preventing restenosis that can result from the angioplasty procedure.

It thus is an object to provide a method for interfering with the events that occur as a result of the normal process of the binding of platelets to the site of an injury.

Another object of the invention is to provide a method for inhibiting the release of platelet substances such as platelet derived growth factor.

Another object of the invention is to provide methods and products for inhibiting restenosis following angioplasty.

Another object of the invention is to provide methods and products for inhibiting tissue adhesion such as results from surgery.

Another object of the invention is to provide methods and products for experimental model systems for testing the role that platelets play in various physiological pathways.

These and other objects will be clear to those of ordinary skill in the art with reference to the following detailed description of the invention.

DETAILED DESCRIPTION OF THE INVENTION

The invention relates in a broad aspect to inhibiting platelets from binding to the site of an injury. It is known that platelets bind to subendothelial tissue that is exposed as a result of trauma, surgery, or disease. Upon binding, platelets release various substances. These substances can have undesirable health consequences in many instances. The invention thus provides methods and products for occupying the sites to which platelets normally bind. Normal circulating platelets then are blocked from binding to such sites and inhibited from releasing platelet substances that may cause undesirable health consequences.

A platelet substances as used herein means any substance released by a platelet as a result of platelet-binding. Such substances include those contained in lysosomes, dense granules and alpha granules. They in particular include: endoglycosidases and heparin cleaving enzyme (from lysosomes); calcium, seratonin and adenosine diphosphate(from dense granules); and yon Willebrand's factor, fibronectin, thrombospondin, platelet factor IV β thromboglobulin, osteonectin and platelet derived growth factor (alpha granules). They also include other substances contained in platelets, including pharmacologically vasorestrictive monoamines such as histamine and epinephrine.

The products used to block platelet binding sites are platelet binding-site agents. As used herein, "platelet binding-site agent" refers to any agent that binds to the site to which platelets bind as a result of injury, and in particular, injury to a vessel. Specifically excluded from this definition, of course, are platelets themselves.

Platelet binding-site agents can be derived from platelets or precursors thereof or can be synthesized from isolated starting materials. If derived from platelets, the platelet binding-site agent comprises a platelet that is substantially free of at least one platelet substance. If synthesized, the starting materials may include material isolated from platelets or other sources, recombinantly produced material, as well as chemically synthesized material.

The preferred platelet binding-site agent will depend upon the particular use to which the agent is being directed. For example, if the agent is being used to block platelet binding and inhibit the release of growth factor, then it should be substantially free of growth factor. "Substantially free of" as used herein embraces both a total absence of as well an effective absence of a particular substance. An effective absence means an amount insufficient to produce the level of biological activity characteristic when normal platelets bind to a site of injury. Instead, reduced biological activity would occur. Thus, the platelet binding-site agents useful herein are substantially free of a selected substance that is normally released by a platelet upon binding.

Platelet binding-site agents can be produced by treating normal platelets, or precursors thereof, in order to eliminate the production of the desired platelet substance. For example, precursors of platelets can be genetically engineered to be defective in a particular gene product. This could be accomplished for example by producing a recombinant, totipotent stem cell that has a gene knocked-out via homologous recombination or that has a gene inactivated by interfering with transcription or translation (e.g. using antisense technology). The preferred genetically engineered platelet is one that does not produce platelet derived growth factor. Techniques for producing such recombinant platelets are known to those of ordinary skill in the art. Thus, one type of platelet binding-site agent is a platelet that is substantially free of a selected platelet substance, but is otherwise normally constituted.

One preferred platelet binding-site agent is prepared according to the various procedures described in U.S. patent application Ser. No. 07/786,056, filed on Oct. 31, 1991, the disclosure of which is incorporated herein by reference. This patent application describes a method for synthesizing microvesicles with platelet-like membranes. The synthesis involves forming such microvesicles by mixing isolated phospholipid with isolated platelet glycoprotein. Such mixtures can be formed into microvesicles that have some of the properties of platelets. The membranes of the formed microvesicles can include, or exclude, any selected platelet glycoprotein, but preferably include one that mediates the binding of the microvesicle to the subendothelial tissue at the site of an injury. The formed microvesicles also define a compartment that may contain any selected material, as discussed below.

Platelet binding-site agents also include phospholipids alone or glycoproteins alone, provided that the phospholipid (or phospholipid composition) or glycoprotein is capable of binding to platelet-binding sites. Platelet-binding site agents also include platelet membrane particles. A platelet membrane particle comprises at least one phospholipid and at least one glycoprotein. Thus, as will be readily understood in connection with the discussion below, the platelet binding-site agents useful according to the invention can be prepared without using platelets as a starting material.

The term platelet glycoprotein is intended to mean glycoprotein associated with platelet membranes. Such glycoproteins can be isolated from platelet membranes or can be the product of genetic engineering. A preferred source for glycoproteins is either fresh or outdated human platelets. Platelet glycoproteins also may be obtained from nonhuman mammalian species, including primates, cows, horses, sheep, goats, rabbits, swine, dogs, cats and rodents.

Glycoproteins may be isolated from platelets by first centrifuging and washing the platelets. The platelets then may be suspended in a Triton detergent solution, and the suspension then is centrifuged over sucrose cushions to separate the proteins. Glycoprotein then can be purified by affinity chromatography over a wheat-germ lectin column and eluted with N-acetyl-glucosamine.

Glycoprotein Ib is believed to be important in platelet adhesion. It may function to maintain the integrity and normal physiology of the blood vessel and endothelium, and it is believed to be involved in preventing blood leakage from the blood vessel by participating in the formation of the initial plug. The glycoprotein complex IIb/IIIa is believed to function as a fibrinogen receptor, necessary for platelet aggregation and deposition of fibrin, which takes place after the initial plug is formed in a leaky vessel. Thus, the platelet binding-site agents of the invention can include GPIb, GPIIb, GPIIIa, GPIIb/IIIa complex, or any combination of the foregoing. Preferably, the platelet binding-site agent has a glycoprotein selected for its ability to adhere to blood vessels which have been injured. The glycoprotein which is believed to function in that capacity is glycoprotein Ib.

Molecules or adhesion proteins originating in. other species may be identified that are substantially the same in structure and/or function as the particular glycoproteins described above. Glycoproteins may also be obtained through recombinant technology or by protein chemistry. The platelet binding-site agents of the present invention thus may contain proteins that are not normally found in platelet membranes or that are derived from nonplatelet sources.

The phospholipids used may be derived from fresh or outdated platelet membrane, from other blood cell membrane such as red blood cells or other lipid sources. Preferably, the phospholipids are similar or identical to those that are present in human platelets. To prepare the phospholipids from blood samples, platelets can be separated from other blood components by centrifugation. The intact platelets can be disrupted by repeated freezing and thawing. Phospholipids are extracted from the platelet membranes using solvent systems and recovered by drying the lipid containing solvent. A preferred solvent system is hexane-isopropenol. The preferred phospholipids are phosphatidylinositol, phosphatidylethanolamine, phosphatidylserine, phosphatidylcholine and sphingomyelin.

The platelet binding-site agents can be prepared to contain glycoproteins and phospholipids that are present in different concentrations than that normally found in platelet membranes. Thus, the platelet binding-site agents may be prepared to optimize their ability to inhibit the binding of circulating platelets to the site of an injury and the consequent release of platelet substances. It should be noted that the selection and relative amounts of the different phopholipids in the platelet membrane vesicles can influence the incorporation of glycoproteins into those vesicles. It further should be noted that the ratio of glycoprotein to phospholipids in the membrane vesicles is related to the hemostatic function of the product. Therefore, if a hemostatic function is desired, the phospholipid composition should be selected to incorporate sufficient glycoprotein into the vesicles to promote hemostasis. A preferred phospholipid to glycoprotein ratio is 1:10 (wt/wt). It should be understood, however, that a maximum hemostatic function is not necessary to achieve the purposes of this invention and, in certain instances, may interfere with obtaining the complete benefits of this invention. The relative amounts of glycoprotein and phospholipid, the particular glycoproteins and phospholipids selected and the amount of hemostatic function of the platelet binding-site agent will depend upon the particular use to which the invention is being directed, and can be determined by one of ordinary skill in the art.

The most preferred platelet binding-site agent is prepared according the procedure described in U.S. Pat. No. 5,185, 160, issued Feb. 9, 1993, the disclosure of which is incorporated herein by reference. This patent describes methods and products relating to derivatives of platelets. Briefly, whole platelets (outdated or fresh) are heat treated to destroy virus and sonicated to form microvesicles. They also are frozen, thawed and washed repeatedly. The platelet membrane microvesicles that result are free of lysosomes, dense granules and alpha granules. They in particular are substantially free of platelet derived growth factor, seratonin, GPIIb/IIIa complex, purine nucleocide phosphorolase, coagulation factors V, VIII, IX and X and thrombospondin. In general, they are substantially free of platelet substances contained in lysosomes, dense granules and alpha granules. Furthermore, these microvesicles are substantially nonalloimmunogenic.

As mentioned above, platelet binding-site agents are useful in preventing platelets from binding to subendothelial tissue and from causing adverse health consequences. They can be used, for example, in the treatment of any arterial occlusion, including coronary, renal, iliac and vertibral artery occlusions. They also can be used in the treatment of lesions to blood vessels. Virtually any situation that involves damage to a blood vessel and/or exposure of platelets to subendothelial connective tissue can be an indication for treatment with platelet binding-site agents. One particular application is in connection with surgery to prevent post-surgical tissue adhesion. Another application is for treating Capilary Leak Syndrome, such as is associated with Adult Respiratory Distress Syndrome to prevent capilary leak and edema and the problems associated therewith.

The preferred use is in connection with coronary angioplasty. Angioplasty procedures and in particular laser procedures, mechanical atheromectomy procedures and percutaneous transluminal dilatation balloon procedures lessen an occlusion, but typically denude the endothelial lining at the site of the angioplasty and expose the subendothelial tissue to platelets. While not wishing to be bound to any particular theory, it is believed that platelets then bind to this tissue and, among other things, release platelet derived growth factor. This in turn stimulates the proliferation of smooth muscle cells and contributes to restenosis.

According to the invention, platelet binding-site agents are delivered to the site of the angioplasty to bind to and occupy the sites of platelet-binding. The sites then are unavailable for normal platelet binding and consequent release of platelet substances including growth factors. By inhibiting the release of growth factors, smooth muscle cell proliferation is inhibited. This lessens or eliminates the chance of restenosis.

Because of the high concentration of normal circulating platelets, systemic delivery of the platelet binding site agent would not be effective in preventing binding of normal platelets to the subendothelial space. Therefore, the various applications of the invention require local or site-specific delivery of the agents to ensure saturation of the binding sites with the binding site agents. In connection with angioplasty, various catheters exist for achieving this end. For example, double or triple balloon catheters of the type that can form a chamber within an artery between a pair of balloons can be used to isolate the injured area and supersaturate the chamber with platelet binding-site agent. A particularly preferred catheter would be one that is capable of flushing the circulating platelets from the chamber formed by the balloons prior to the angioplasty procedure and prior to the introduction of the platelet binding-site agent into the chamber.

Other catheters exist which permit a slow weeping fluid from the dilatation balloon via openings in the balloon when the balloon is pressurized. This would result in a thin layer of fluid containing the platelet binding-site agent between the balloon and the site of the injury, the fluid being expressed directly onto the site of the injured vessel wall at the time of the dilatation. Other mechanisms for site-specific delivery during an angioplasty procedure will be known to those of ordinary skill in the art, and the invention is not intended to be limited to any particular device selected. It also should be noted that a platelet binding-site agent could be coated onto the outer surface of the dilatation balloon thereby forcing the platelet binding-site agent onto the site of injury during the dilatation procedure.

Exemplary angioplasty devices are described in U.S. Pat. Nos. 4,573,966 (Mar. 4, 1986), 4,636,195 (Jan. 13, 1987), 4,994,033 (Feb. 19, 1991) and 5,049,132 (Sep. 17, 1991), the disclosures of which are incorporated herein by reference.

Another preferred use of the invention is in preventing or reducing post-surgical tissue adhesion. A major complication of certain surgical procedures is tissue adhesion. To avoid or reduce this complication, platelet binding-site agents may be applied to tissues during or at the end of surgery as a bathing solution or in a more viscous coating such as an ointment. The platelet binding-site agents then would occupy the platelet binding sites exposed to blood as a result of the surgery, thereby preventing or lessening the amount of platelet substances that otherwise would have been released (e.g. growth factor, etc.). This in turn would reduce the amount of cell proliferation and connective tissue deposition, thereby lessening undesirable tissue adhesion.

As described above, it is important that the platelet binding-site agent occupy platelet binding-sites to prevent platelet binding. Thus, the modes of delivery useful in connection with this invention are local or site-specific. "Local" or "site-specific" means a mode of delivery that permits substantial occupation of the available platelet binding-sites at the site of an injury. Examples of such modes of delivery have been described above. The particular mode of delivery will depend upon the particular condition being treated, and selection of an appropriate mode can be accomplished by those of ordinary skill in the art without undue experimentation. Systemic delivery, however, is specifically excluded from the term "local" and "site-specific".

The preferred platelet binding-site agent when prepared as described above happens to have strong hemostatic capability. It will be understood by those of ordinary skill in the art that such capability may be unnecessary for certain uses of the invention. Likewise, the preferred material has been used to stop bleeding in patients. It should be understood that uses of the platelet binding-site agent according to the invention herein are unrelated to the prior uses of such material for stopping bleeding. Thus, the platelet binding-site agents according to the invention described herein are useful in patients who are otherwise substantially free of indications relating to blood loss. An example of such a patient is one undergoing an angioplasty procedure. Another example would be a surgical procedure wherein the blood loss as a result of Surgery is not sufficient to require a platelet-containing blood substitute.

The platelet binding-site agent may also comprise other therapeutic agents. Such therapeutic agents may contribute additional or unique features to the platelet binding-site agent. In the case of formed microvesicles, the therapeutic agent may be carried on the membrane, incorporated into the membrane or contained inside the microvesicle. In one embodiment of the invention, the platelet membrane vesicles may contain therapeutic substances entrapped within the lumina of the individual vesicles to be available at the site of the injury when the vesicles bind to platelet binding-sites. Therapeutic substances refer to agents which achieve a medically desirable result when administered to a subject. The therapeutic substances can encompass many pharmaceutical products including anticoagulants, antibiotics, vasoconstrictive agents and the like. Serotonin, aspirin and heparin are in particular contemplated.

An important feature of the preferred platelet binding-site agents is that they can be stored for a long period of time and can be produced from outdated, nonhuman or genetically engineered materials which ensure that the product can be available in large supply and at a reasonable cost.

A further advantage of the use of platelet membrane vesicles is that components of the vesicles can be made viral free. Viral contamination, particularly with hepatitis and human immunodeficiency viruses, is a significant risk factor in treating patients with blood products. The compositions of the present invention may be produced from nonhuman sources precluding the contamination of the source material with many viruses that are infectious to humans.

The platelet binding-site agents are applied in effective amounts. An effective amount is a dosage of the product sufficient to provide a medically desirable result. The effective amount will vary with the particular condition being treated, the age and physical condition of the subject being treated, the severity of the condition, the duration of the treatment, the nature of the concurrent therapy, the specific route of administration and like factors within the knowledge and expertise of the health practitioner. For example, an effective amount of a platelet binding-site agent would be an amount sufficient to lessen the risk of or prevent altogether restenosis after an angioplasty procedure.

The platelet binding-site agents are prepared in compositions that are pharmaceutically acceptable. A pharmaceutically acceptable composition is a preparation which is relatively nontoxic and innocuous to a patient at concentrations consistent with the effective activity of the platelet binding-site agent. Preferably, any side effects ascribable to the pharmaceutically acceptable preparation do not vitiate the beneficial effects of the active ingredient. Typically, the pharmaceutically acceptable preparation includes a carrier, diluent or exipient which is compatible with the components of the formulation. Nontoxic is intended to include substantially nontoxic, e.g. the agent may have a minimal level of toxicity which does not cause a significant harm to the patient. Suitable pharmaceutical preparations include isotonic saline, polyethaline glycol, Ringer's solution, and oils and ointments formed from synthetic mono- or diglycerides or fatty acids.

The preparation is intended to be sterile. By sterile preparation, it is meant a preparation that is free of detectable microorganisms, including bacteria, viruses, fungi and protozoa. The preparation preferably is a sterile aqueous preparation which is isotonic with the blood of the recipient. Such a preparation may be formulated according to known methods using suitable dispersing or wetting agents and suspending agents.

The invention also contemplates the use of platelet binding-site agents in experimental model systems to determine the role that a particular platelet substance plays in mediating the repair of an injury to a vessel or mediating an adverse health consequence occurring as a result of an injury to a vessel. An injury to a blood vessel of an animal is induced experimentally, for example by scraping the endothelial lining of a vessel at a particular site. A platelet that is substantially free of a particular platelet substance, but preferably is otherwise normal, then is applied to the site of the injury. The application may be local, or may be systemic the animal has been previously depleted of normal circulating platelets. Then the animal's response to the injury and treatment is monitored and compared to control animals that do not receive the platelet binding-site agents.

The same type of experimental model system can be used in the preparation of synthetically formed microvesicles (from isolated phospholipids and/or glycoproteins) to determine which platelet binding-site agent has the most beneficial effect when applied to the site of a particular type of injury. Additional features of the present invention will be apparent from the following examples:

EXAMPLE I

Preparation of a platelet binding-site agent from platelet concentrates

One method for preparing a platelet binding-site agent having an absence of growth factor is set forth below.

Freshly-collected, stored (one to five days at 20°–25° C.) or outdated (beyond five days at 4° C.) platelet concentrates (50-60 ml/concentrate) were pooled in 600 ml blood bags (Fenwall transfer pack unit, 4R2023, Fenwall Laboratories, Deerfield, Ill.) via sterile plasma transfer sets (Fenwall 4C2243, Fenwall Laboratories, supra). Each bag contained a total of 500–600 ml of platelet concentrates (hereinafter, 600 ml unit). The 600 ml units were centrifuged at 1,000 rpm for 11 minutes at 22° C. to remove contaminating red and white blood cells (PR7000, International Equipment Company, Needham Heights, Mass.). The supernatants, which contained the platelets, then were transferred to new 600 ml blood bags and centrifuged at 3,000 rpm for 25 minutes at 22° C. to separate platelets from plasma. Platelet-poor plasma was expressed and each of the resulting platelet pellets was gently resuspended in 20 ml of an 0.9% NaCl solution (physiological saline), diluted to a final volume of 100 ml with additional saline, and then pooled in 300 ml blood bags (three 100 ml samples per bag corresponding to three original 600 ml units). The resuspended platelets again were pelleted by centrifugation at 3,000 rpm for 20 minutes at 22° C. The supernatant was removed and the platelet pellet was washed twice with physiological saline by repeated resuspension and centrifugation.

The washed platelets were finally resuspended in physiological saline (25 ml per each 600 ml unit) and disrupted by repeated freezing (at −80° C. for at least six hours) and thawing (at 25° C. for at least one hour), three times. The frozen and thawed suspension was diluted with physiological saline (100 ml per each 600 ml unit) and centrifuged at 3,000 rpm for 30 minutes to collect a platelet ghost pellet. This platelet ghost pellet was resuspended in physiological saline (100 ml per each 600 ml unit) and washed twice by repeated resuspension and centrifugation.

The washed ghost pellet was resuspended in physiological saline (40–50 ml per each 600 ml unit) and heated at 60° C. for 20 hours in a water bath. Alternatively, the platelet ghost suspension may be heated to 100° C. for five minutes. These conditions are sufficient to inactivate any viral contaminants. A gross precipitate developed during the heat treatment. This heat-treated, platelet ghost suspension then was homogenized in a sonicator (ultrasonic processor Model W-385, Heat Systems, Inc., Farmingdale, N.Y.) using a ½" disruptor horn in a flow cell (Model 800B, Heat Systems). The sonicator system was flushed first with nitrogen prior to injection of the platelet ghost suspension. The suspension was sonicated by pulsing at 20 kHz for 5 minutes and 43 seconds (2 second cycle, 1.4 seconds on, 0.6 seconds off) with output control setting at "4" to produce double amplitude of 48 micrometers. The sonicated preparation next was centrifuged at 3,000 rpm for 30 minutes at 22° C. to separate the precipitated material from the formed platelet membrane microvesicles which remain in the supernatant. The supernatant was removed and stored in sealed containers at either 4° C., −20° C. or −80° C. under nitrogen, or stored lyophilized under nitrogen. Unless otherwise indicated, microvesicles stored at 4° C. were used in the following procedures.

The platelet microvesicle fraction prepared as described above was free of active virus. It also was substantially free of platelet ghosts, with greater than 80% of the microvesilces being less than 600 nanometers in diameter and greater than 95% less than 1,000 nanometers. The average diameter of the microvesicles prepared from newly outdated platelets (within two weeks after outdating) for 7 different preparations was between 300 and 400 nanometers. The mean diameter for the 7 preparations was 341 nanometers.

The platelet microvesicle fraction also was substantially free of seratonin, GPIIb/IIIa (a surface glycoprotein), purine nucleoside phosphorylase, coagulation factors V, VIII, IX and X, and thrombospondin (an alpha granule component). On the other hand, GPIb (another surface glycoprotein) was present and Beta-glucuronidase (a lyzosomal marker) also was detectable (about 25% as a percent of lysate).

The composition of the platelet microvesicle fraction was determined in two different sets of experiments for certain components and is presented in Table I:

TABLE I

| | PERCENT OF COMBINED WEIGHT (W/W) | | | |
|---|---|---|---|---|
| EXPT. | CARBO-HYDRATE | PHOSPHO-LIPID | PROTEIN | CHOLES-TEROL |
| N = 4 | 3.3 ± 0.14 | 30. ± 0.9 | 57.8 ± 0.9 | 9(assumed) |
| N = 8 | 2.6 ± .3 | 30.1 ± 2.5 | 53.2 ± 1.7 | 9.9 ± .9 |

The composition of the phospholipid portion of the preparation was determined in two different sets of experiments and is shown in Table II:

TABLE II

| | PERCENT OF COMBINED PHOSPHOLIPID (W/W) | | | | |
|---|---|---|---|---|---|
| EXP. | PI | PS | PE | PC | SP |
| N = 4 | 5.8 ± 1.0 | 10.1 ± 0.9 | 22.5 ± 1.5 | 45.8 ± 4.0 | 15.4 ± .7 |
| N = 8 | 6.8 ± .5 | 12.2 ± .7 | 23.8 ± 2.1 | 40.6 ± 2.3 | 16.6 ± 1.5 |

PI: phosphatidylinositol
PS: phosphatidylserine
PE: phosphatidylethanolamine
PC: phosphatidylcholine
SP: sphingomyelin The final product and intermediates also were tested in immunological dot assays for the presence of HLA antigens (Class I). HLA antigens were present in the washed, intact platelet preparations, the platelet lysate, the supernatant from the platelet lysate, and the platelet membrane ghost fraction. HLA antigens were not detectable in a heated platelet membrane ghost fraction or in the final product.

The final product and various intermediates further were tested in immunological dot assays for the presence of GPIb. All samples tested, including those heat treated, showed the presence of GPIb.

EXAMPLE II

Preparation of Platelet Glycoproteins

Platelet glycoproteins were prepared by modification of a procedure originally described by Wicki and Clemetson (1987). Outdated platelet concentrates were pooled and centrifuged at 350 g for 10 min to remove the red blood cells. The resultant platelet rich plasma was centrifuged again at 1500 g for 15 min to give a pellet containing platelets, which were suspended in 10 ml per original platelet unit in buffer A (4.8 mM glucose, 3 mM KCl, 100 mM NaCl, 10 mM EDTA, 30 mM sodium citrate, pH 6.5). This suspension was centrifuged at 1500 g for 15 min, and the resultant pellet was washed twice with buffer B (10 ml per original platelet unit; 30 mM glucose, 120 mM NaCl, 10 mM EDTA, 5 mM sodium citrate, pH 6.5) and once with buffer C (10 ml per original platelet unit; 134 mM NaCl, 10 mM EDTA, 10 mM Tris/HCl, pH 7.4). The platelet pellet than was solubilized in buffer D (124 mM NaCl, 20 mM EDTA, 2 mM phenylmethysulfonyl fluoride, 2 mM N-ethylmaleimide, 2% Triton X-114, 10 mM Tris/HCl, pH 7.4) with a volume equivalent to the pellet. The mixture was stirred at room temperature for 30 min and centrifuged at 2500 g for 2 hours at 4° C. The supernatant was further clarified by ultra-centrifugation at 100,000 g for 1 hour at 4° C. to give a clear solution for the following sucrose cushion centrifugations. Twenty ml aliquots of 6% sucrose in buffer E (154 mM NaCl, 1 mM EDTA, 0.06% Triton X-114, 10 mM Tris/HCl, pH 7.4) were introduced into 50 ml centrifuge tubes and were warmed to 35° C. and carefully overlayered with 20 ml of clear supernatant from the ultracentrifugation. After spinning at 1000 g for 10 min at 30° C., the top layers of all the tubes were collected and enriched with additional 1% Triton X-114 (w/w). The solution, which turned cloudy after being warmed to 35° C., was again overlayered and centrifuged with 6% sucrose cushions as above. The top layers of all the tubes were collected (as 2nd SC Top) and contained platelet proteins.

The crude glycoproteins were further purified by affinity chromatography with wheat germ lectin (WGL)-Sephrose 4B which primarily interacts with several platelet glycoproteins such as GPIb, GPIa, and GPV (Clemetson et al., 1977). Fractions eluted from the WGL column were collected and monitored by dot assay using monoclonal antiglycocalicin (P6D9G) as primary antibody, and only those showing positive results were pooled, concentrated, dialyzed and filtered for further use.

Wheat germ lectin (WGL) Sephrose 4B (1.5 mg WGL/ml gel) was prepared from CNBr-activated Sephrose 4B according to the procedure from the manufacturer (Pharmacia). The solubilized platelet protein solution (50–80 ml of 2nd SC Top) was applied to a column of WGL-Sephrose 4B (2.5×8 cm) equilibrated in 20 mM Tris HCl, pH 7.4. After the flow through and extensive washing, the bound material was eluted with 2.5% N-acetylglucosamine in the same buffer. Fractions, which showed positive in dot assay using monoclonal antiglycocalicin as primary antibody, were pooled, concentrated with Amocon concentrators and further dialyzed against 20 mM Tris/HCl, pH 7.4. The monoclonal antiglycocalicin was made by standard methods as are well known to those skilled in the art. The purified glycoproteins were then filtered (0.2 um filter) and stored at −80° C.

The concentrated and dialyzed glycoproteins from the WGL affinity column may be further purified by anion exchange chromatography with a DEAE-Sepharcel column (2.5×27 cm) equilibrated with buffer F (30 mM NaCl, 20 mM MeS/HCl, pH 5.5). The column was eluted with a 200 ml gradient of 0.03–0.6M NaCl in buffer F followed by 1M NaCl in buffer F. The fractions were collected and analyzed by $OD_{280}nm$ and dot assay. Those containing GPIb complex were pooled, concentrated, dialysed and filtered for further use.

EXAMPLE III

Preparation of Platelet Membrane Lipid Extract

The platelet membrane lipids were extracted from platelet membranes. To produce platelet membranes, 600 ml of pooled platelet concentrates were centrifuged at 1,100 rpm for 11 minutes at 22° C. to remove contaminating red and white blood cells. The supernatant fluid portions, containing the platelets, were centrifuged at 3,000 rpm for 25 minutes at 22° C. to separate platelets from plasma. After discarding the platelet-poor plasma, the platelet pellets were resuspended in 20 ml of 0.9% saline, and diluted to a final volume of 100 ml. The resuspended platelets were pelletted again by centrifugation at 3,000 rpm for 20 minutes at 22° C. The wash was repeated twice more. After resuspension, the washed platelets were disrupted by repeated freezing (at −80° C. for at least six hours) and thawing (at 25° C. for at least one hour), three times. The frozen and thawed suspension was diluted with physiological saline (100 ml per each 600 ml unit) and centrifuged at 3,000 rpm for 30 minutes to collect a platelet ghost pellet. This platelet ghost pellet was resuspended in physiological saline (100 ml per each 600 ml unit) and washed twice by repeated centrifugation and resuspension.

Several of the examples below refer to the use of an Infusible Platelet Membrane (IPM) preparation as a membrane source in the experimental protocols. IPM is a preparation of isolated native platelet membranes, formed into microvesicles. Phospholipid analysis shows that the phospholipid compositions of both native platelet membranes and of IPM are identical. To prepare IPM, the platelet membrane preparation of the preceding paragraph was heated and then sonicated according to the method as described in U.S. Pat. Nos. 5,332,578 and 5,185,168.

A mixture of hexane/isopropanol (HIP, 3:2 v/v) is an effective solvent system for the extraction of phospholipids from cells and cell fractions (Saunders and Horrack, 1984). A mixture of 4 ml of IPM and 4 ml of HIP was vigorously mixed by vortex for 1 min in a screw-capped tube. A total of 80 ml of IPM in 20 tubes was processed. After the centrifugation (2500 g for 10 min) the top organic layer of each tube was collected as HIP/Top. The content of phospholipids was determined by HPLC and an aliquot of the lipid extract (HIP/Top) was dispensed into 15 ml tubes (each with 4 mg of phospholipids), capped tightly and stored at −80° C.

EXAMPLE IV

Preparation of Red Cell Membrane Lipid Extract

A similar HIP extract procedure as described above was employed to prepare the red cell membrane lipids. Red cells were isolated from anticoagulated whole blood by centrifugation. A red cell membrane solution was prepared from red cell ghost in the same manner as that of IPM including heating (60° C. for 20 hours) and sonication.

EXAMPLE V

Preparation of Platelet Membranes Vesicles (PMV) and Red Cell Membrane Vesicles (RCMV)

After being warmed up to room temperature, the tubes containing platelet lipid extract were evaporated to dryness by a shaker/evaporator. The evaporation process was carried out under vacuum with shaking at 55°–60° C. to ensure a uniform lipid coating on the walls of the glass tubes. An aliquot of 3.65 ml of the protein solution prepared as described above (in 154 mM NaCl, 20 mM Tris/HCl, pH 7.4) was immediately added to the dry lipids and vigorously mixed by vortex for 3 min. The membranes prepared as such appeared as a homogenous milky solution which can be stored at 4° C. for further use. This procedure was also employed for preparing the red cell membranes except that the lipid extract was from red cells instead of platelets.

EXAMPLE VI

Administration of a platelet binding-site agent to site of angioplasty

In the practice of this invention, a three balloon catheter is employed. The catheter is guided by standard procedures which may include the use of a flexible probe, a guidewire and/or a fluoroscope to a position overlaying the original site of the plaque body at the stenosis.

The catheter has three balloons in a spaced relationship, two outer chamber-forming balloons and a dilatation balloon positioned in between the outer balloons. The dilatation balloon is positioned at the site of the stenosis; the two outer balloons are on either side of the stenosis and inflated to define a chamber containing the stenosis.

A platelet binding-site agent prepared as in Example I is suspended in a suitable pharmaceutical carrier (isotonic saline). The platelet binding-site agent is substantially non-toxic and the concentration of the platelet binding-site agent is expected to have a wide range of acceptable dosages. A preferred concentration of a platelet binding-site agent is 10 to 15 μmg/ml in isotonic saline. The platelet binding-site agent is forced under pressure through a conduit in the catheter which conduit has an opening within the chamber. At the same time, blood within the chamber is flushed from the chamber and replaced with platelet binding-site agent.

Then the third balloon is expanded under pressure to dilate the stenosis and to further compel the platelet binding-site agent to the arterial wall. The chamber-forming balloons are held in place for 5–60 seconds to hold the platelet binding-site agent in the chamber and provide time for the platelet binding-site agent to occupy platelet binding sites within the chamber.

Following application of the platelet binding-site agent, all the balloons of the catheter are deflated and the catheter is removed. The platelet binding-site agent adheres to the injured site, in the manner of a platelet. However, the platelet binding-site agent has no growth factor activity and therefore does not contribute to the proliferation of smooth muscle cells and other cells of the arterial wall. The platelet binding-site agent occupies the platelet binding sites preventing the binding of platelets which release growth factor activity. Thus, restenosis is less likely to occur following administration of the platelet binding-site agent.

Thus, while preferred embodiments of the invention have been described, the present invention is capable of variation and modification and, therefore, the present invention should not be limited to the precise details set forth, but should include such changes and alterations as fall within the purview of the following claims.

What is claimed:

1. A method for inhibiting the attachment of platelets to a site of an injury, comprising:
   administering to a subject that has sustained an injury an effective amount of a platelet binding-site agent, wherein the platelet binding-site agent is a non-platelet.

2. A method as claimed in claim 1 wherein the platelet binding-site agent is administered locally to the site of the injury.

3. A method as claimed in claim 2 wherein the platelet binding-site agent is administered to the site of an injury resulting from surgery.

4. A method as claimed in claim 3 wherein the platelet binding-site agent is administered locally to an internal surface of the subject.

5. A method as claimed in claim 2 wherein the platelet binding-site agent is administered to the site of an injury on a blood vessel.

6. A method as claimed in claim 2 wherein the platelet binding-site agent is administered to a subject with an arterial occlusion in conjunction with treatment of said occlusion.

7. A method as claimed in claim 2 wherein the platelet binding-site agent is administered to a subject with a coronary artery occlusion in conjunction with dilatation balloon angioplasty.

8. A method as claimed in claim 1, 2, 3, 4, 5, 6 or 7 wherein a platelet binding-site agent that is free of growth factor activity is administered to inhibit the release in vivo of platelet derived growth factor.

9. A method as claimed in claim 1, 2, 3, 4, 5, 6 or 7 wherein a platelet binding-site agent that is free of adhesion molecules is administered to inhibit cell adhesion at the site of the injury.

10. A method as claimed in claim 6 wherein the platelet binding-site agent is administered to a patient via a catheter.

11. A method as claimed in claim 1, 2, 3, 4, 5, 6 or 7 wherein the platelet binding-site agent is in a preparation containing platelets, or membrane fragments thereof, that have been treated to remove growth factor and adhesion molecule activity.

12. A method as claimed in claim 1, 2, 3, 4, 5, 6 or 7 wherein the platelet binding-site agent is in a preparation that contains isolated platelet membrane microvesicles.

13. A method as claimed in claim 1, 2, 3, 4, 5, 6 or 7 wherein the platelet binding-site agent is formed by mixing an isolated preparation of phospholipid with an isolated preparation of glycoproteins, the glycoproteins being selected from the group consisting of: glycoprotein Ib, glycoprotein IIb and glycoprotein IIIa.

14. A method as claimed in claim 1, 2, 3, 4, 5, 6 or 7 wherein the platelet binding-site agent comprises a glycoprotein that is a constituent of platelet membranes.

15. A method as claimed in claim 1, 2, 3, 4, 5, 6 or 7 wherein the platelet binding-site agent comprises a phospholipid that is a constituent of platelet membranes.

16. A method as claimed in claim 7 wherein the platelet binding-site agent is administered using an apparatus for performing dilatation balloon angioplasty.

17. A method as claimed in claim 7 wherein the platelet binding-site agent is administered as a coating upon a dilatation balloon.

* * * * *